United States Patent [19]
Lee

[11] 4,401,517
[45] Aug. 30, 1983

[54] VAPOR-LIQUID EXTRACTIVE DISTILLATION WITH DIALKYL SULFONE/WATER COMBINATION

[75] Inventor: Fu-Ming Lee, Bartlesville, Okla.

[73] Assignee: Phillips Petroleum Company, Bartlesville, Okla.

[21] Appl. No.: 323,772

[22] Filed: Nov. 20, 1981

[51] Int. Cl.³ ............................ B01D 3/40; C07C 7/08
[52] U.S. Cl. ........................................ 203/53; 203/57; 203/85; 585/805; 585/807; 585/856
[58] Field of Search ....................... 203/53, 57, 96, 85; 585/804–807, 856, 864, 857

[56] References Cited

U.S. PATENT DOCUMENTS

| | | | |
|---|---|---|---|
| 2,033,942 | 3/1936 | Kurtz | 208/322 |
| 2,357,028 | 8/1944 | Shiras et al. | 203/58 |
| 2,407,820 | 9/1946 | Durrum | 585/805 |
| 2,831,039 | 4/1958 | Nevitt | 585/856 |
| 2,849,514 | 8/1958 | Nevitt | 585/856 |
| 2,884,360 | 4/1959 | Bloom et al. | 203/57 |
| 3,070,518 | 12/1962 | Nelson et al. | 585/856 |
| 4,024,028 | 5/1977 | Haskell | 203/57 |
| 4,053,369 | 10/1977 | Cines | 203/52 |
| 4,076,595 | 2/1978 | Haskell | 203/57 |

OTHER PUBLICATIONS

Weissberger: Techniques of Organic Chemistry, vol. Distillation; 1965, pp. 430, 431 and 457.

*Primary Examiner*—Wilbur L. Bascomb, Jr.

[57] ABSTRACT

A vapor-liquid extractive distillation process utilizing a dialkyl sulfone containing 4 to 8 carbon atoms per molecule and at least one percent water as the solvent. The process according to this invention is of particular applicability in separating aromatics from nonaromatics in a BTX stream. The solvent system operates particularly well with relatively large amounts of water.

10 Claims, 6 Drawing Figures

EXTRACTIVE DISTILLATION FLOW DIAGRAM

FIG. 1 EXTRACTIVE DISTILLATION FLOW DIAGRAM

RELATIVE VOLATILITY VERSUS SOLVENT
TO HYDROCARBON FEED RATIO

RELATIVE VOLTILITY VERSUS WATER CONTENT IN THE SOLVENT

SOLVENCY VERSUS SOLVENT TO HYDROCARBON FEED RATIO

RELATIVE VOLATILITY OF n- OCTANE TO TOLUENE
IN FULL RANGE SADHC FEED

RELATIVE VOLATILITY OF n - OCTANE TO TOLENE
IN FULL RANGE SADHC FEED

VAPOR-LIQUID EXTRACTIVE DISTILLATION WITH DIALKYL SULFONE/WATER COMBINATION

BACKGROUND OF THE INVENTION

This invention relates to vapor-liquid extractive distillation with a selective solvent.

To separate mixtures, for instance aromatics and non-aromatics by extractive distillation, a third component, a selective solvent can be added to the mixture to alter the relative volatility of the original constituents, thus improving the separation.

The utility of dialkyl sulfones in solvent extraction has been long recognized in the art. It has also been recognized that selective solvents may be blended with co-solvents including water. Water is particularly useful in many solvents in which it is at least partially miscible because it can reduce the boiling point of high boiling point solvents, reduce the freezing point of high freezing point solvents and increase the selectivity or separation factor of the components to be separated. This latter desirable characteristic is generally gained at a price, however, in the loss of solubility of the components to be separated in the selective solvent.

The improvement in separation factor gained by the use of water or any other co-solvent in a selective solvent system is quite unpredictable. For example, in U.S. Pat. No. 2,831,039, Table 2, separation factor for toluene-heptane in methyl ethyl sulfone is increased from 14.8 to 22.4 by the addition of 5 percent water while the same factor for methyl n-propyl sulfone is increased from 3.0 to only 3.03 for the addition of 5 percent water from the solvent.

SUMMARY OF THE INVENTION

It is an object of this invention to provide an improved solvent system for aromatic recovery via vapor-liquid extraction;

It is a further object of this invention to provide an improved selective solvent system for vapor-liquid extraction;

It is yet a further object of this invention to improve the economics of a vapor-liquid extraction system; and It is still yet a further object of this invention to provide for the recovery and purification of aromatics from non-aromatics in a hydrocarbon stream.

It is still yet a further object of this invention to provide a selective solvent which has both high selectivity and high solvency.

In accordance with this invention, a vapor-liquid extractive distillation is carried out utilizing a 4 to 8 carbon atom dialkyl sulfone/water mixture as the solvent.

DESCRIPTION OF THE DRAWINGS

In the drawings, forming a part hereof.

DESCRIPTION OF THE PREFERRED EMBODIMENTS

The preferred dialkyl sulfone solvent is di-n-propyl sulfone (DPS). Ethyl propyl sulfone is also suitable. Other suitable sulfones include diethylsulfone, methyl butylsulfone, dibutylsulfone, and other similar dialkyl sulfones containing 4 to 8 carbon atoms per molecule. Dialkyl sulfones are known materials and can be made, for instance by oxidizing the corresponding dialkyl sulfide with nitric acid.

The solvent systems of this invention contains at least about 1 weight percent water, preferably about 4 to 30 weight percent water, more preferably 12 to 20 weight percent based on the weight of sulfone plus water. The preferred amounts of water will depend on the separation to be made and the operating conditions selected.

In accordance with the invention, the solvent system is used in what is known in the art as a vapor-liquid extractive distillation.

The invention is particularly useful for the recovery of the so-called BTX (benzene-toluene-xylene) concentrates or for upgrading refinery streams which are in the motor fuel boiling range such as cat-cracked gasoline or reformates. The invention is particularly useful for the recovery and purification of aromatics from non-aromatics. However, while the primary feedstocks are those containing aromatics, the invention is also useful for separating other hydrocarbon mixtures which are difficult or impossible to separate by ordinary distillation. These include such separations as propylene from propane, butadiene from butylenes and butanes, isoprene from amylenes and pentanes, and other difficult separations where a difference in molecular structure of the components may cause significant differences in activity coefficients exhibited in the presence of the sulfone-water solvent.

Figure 1:
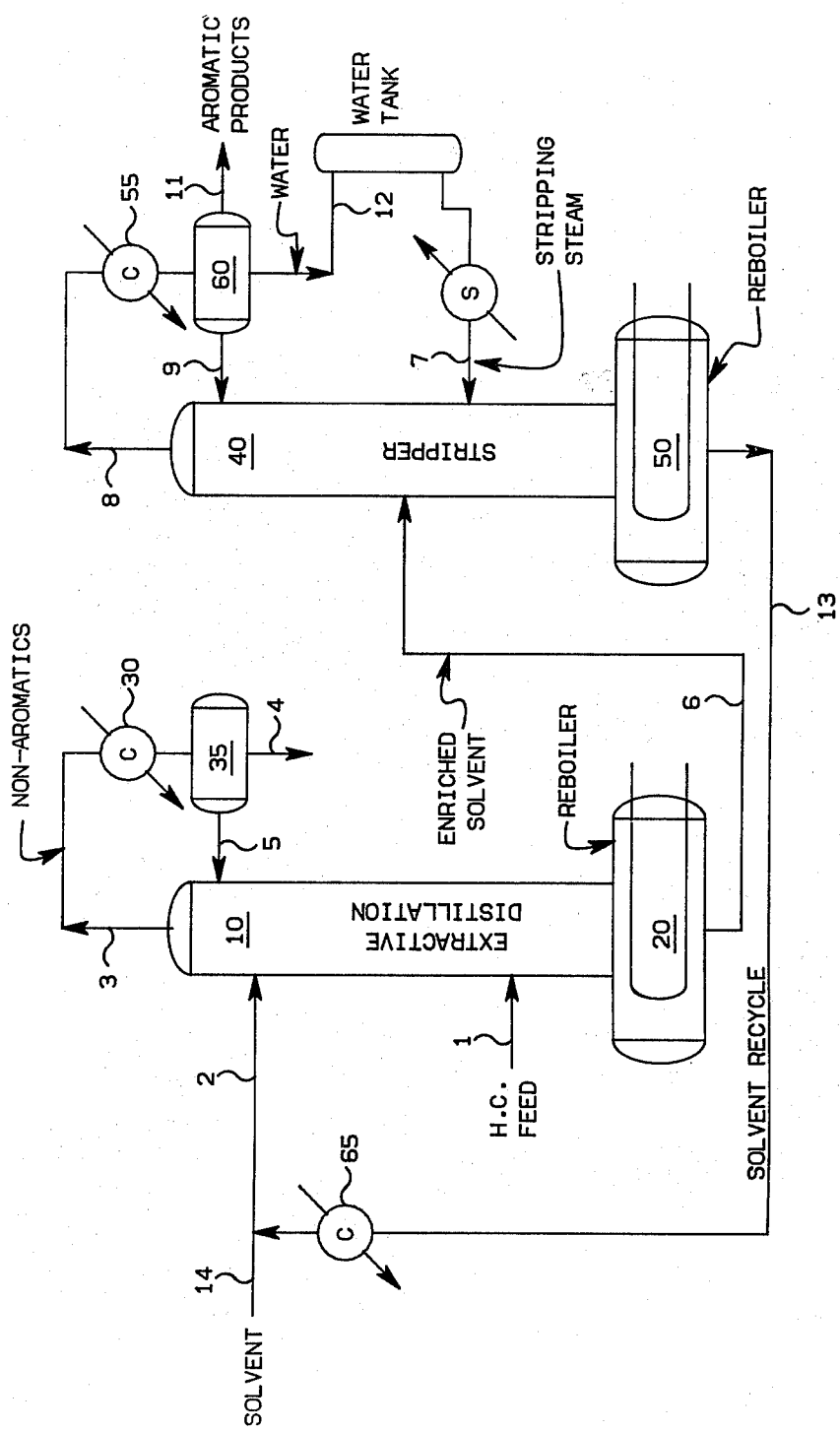
FIG. 1 is a schematic diagram of an extractive distillation plant.

Referring now to FIG. 1, which for exemplification purposes is discussed in terms of a hydrocarbon feed containing aromatics and non-aromatics. The hydrocarbon feed is introduced via line 1 to the vapor-liquid extractive distillation column (EDC) 10. The solvent is fed in near the top of the EDC via line 2. The solvent alters the relative volatility of the original feed constituents, allowing separation of the feed into a column overhead stream 3 rich in non-aromatics and a bottom stream 6 rich in aromatics and solvent. The distillation conditions which are maintained to permit the separation include a proper temperature, which is achieved by heat from column reboiler 20, and proper pressure. The column overhead stream, withdrawn from the EDC 10 via line 3 is passed into column condensor 30, where it is cooled and condensed. From column condensor 30, the condensed stream is passed to the accumulator 35, a first part thereof being removed via line 4 as a product of the process and a second part thereof is returned as reflux to the EDC via line 5.

The extract stream is withdrawn from the EDC 10 via line 6 and fed to the mid-section of stripper 40. The operating conditions in the stripper 40, including temperature and pressure, are such as to separate the feed into stripper overhead comprising mainly aromatics and a bottom stream which is essentially solvent. The necessary heat is supplied to the stripper 40 by a reboiler 50. Stripping steam is fed to the mid-section of stripper 40 to help the separation. The stripper overhead is withdrawn from the stripper 40 via line 8 and directed to condenser 55 which cools and condenses stream 8 before it is passed to accumulator 60. A part of the liquid from accumulator 60 is returned to the stripper 40 as a reflux stream 9 and a part thereof is withdrawn as product via line 11. Water is withdrawn from accumulator 60 via line 12 to a water tank. The stripper bottoms stream withdrawn via line 13 is passed through cooler 65 and then combined with fresh solvent feed from line 14 to form solvent feed stream 2.

One of the most widely used selective solvents for commercial recovery of aromatics is sulfolane. The solvent is relatively inexpensive, stable, high boiling and can be advantageously diluted with minor amounts of water to reduce its boiling and freezing points. In evaluating this invention, the solubility and selectively of DPS have been compared with sulfolane. It has been found that under the various conditions tested that DPS generally has higher hydrocarbon solubility and higher selectivity for aromatics than sulfolane when the two solvents have the same water concentration. Both solvents were diluted with at least a minor amount of water to reduce the normal boiling point of the solvent which is 516° F. (269° C.) for DPS and 545° F. (285° C.) for sulfolane. This lowering of the boiling point serves to reduce energy requirements and to increase solvent stability during stripping operations.

All equilibrium data were obtained in an agitated equilibrium cell, jacketed for temperature control but limited to atmospheric pressure operation. Thus all data were obtained at atmospheric pressure. Hydrocarbon and solvent components were added to the cell, agitated for a sufficient period of time to achieve equilibrium at the test temperature, agitation stopped and the two phases allowed to settle, the phases sampled and analyzed by chromatography.

EXAMPLE I

DPS and sulfolane solvents, each containing 3.56 percent (weight) water, were equilibrated with liquid hydrocarbon feed containing 44.65 percent (molal) n-octane and 55.35 percent toluene at 77° F. (25° C.) at various solvent/feed (S/F) weight ratios with the following results:

| Solvent: | DPS | | | | Sulfolane | | | |
|---|---|---|---|---|---|---|---|---|
| | n-Octane | | Toluene | | n-Octane | | Toluene | |
| S/F | $R_1$ | $E_1$ | $R_2$ | $E_2$ | $R_1$ | $E_1$ | $R_2$ | $E_2$ |
| 1.0 | 60.97 | 39.03 | 33.77 | 66.23 | 97.12 | 2.87 | 72.12 | 27.87 |
| 2.0 | 47.15 | 52.85 | 15.28 | 84.72 | 96.67 | 3.33 | 54.82 | 45.17 |
| 3.0 | 36.75 | 63.25 | 9.03 | 90.97 | 94.07 | 5.93 | 42.67 | 57.33 |

$R_1$, $R_2$—Amount of original n-octane and toluene in raffinate phase, respectively, percent.
$E_1$, $E_2$—Amount of original n-octane and toluene in extract phase, respectively, percent.

It is readily apparent from an examination of the above data that for any S/F ratio tested the amounts of hydrocarbons dissolved in the solvent extracts are much higher for DPS than for sulfolane, thereby indicating the higher solvent capacity for DPS at the same water dilution level.

EXAMPLE II

Vapor-liquid equilibrium data (again at one atmosphere pressure) were obtained by equilibrating the same octane-toluene hydrocarbon feed of Example I with DPS and sulfolane solvents containing various water concentrations, again at various S/F ratios. From the phase compositions relative volatilities were calculated in the usual manner.

It may be noted from the following data that relative volatilities are consistently higher for DPS mixtures. Further, relative volatilities for DPS mixtures increase with increasing water up to around 20 percent water before tapering off while for sulfolane the relative volatilities trend downward with increasing water concentrations after peaking at 3.56% water.

| | Water in | Relative Volatility, $\alpha$ Solvent | |
|---|---|---|---|
| S/F | Solvent, Wt. % | DPS | Sulfolane |
| 0 | — | 0.65 | 0.65 |
| 1 | 0.00 | 1.11 | — |
| 1 | 3.56 | 1.17 | 0.96 |
| 2 | 3.56 | 1.57 | 1.24 |
| 3 | 3.56 | 1.81 | 1.48 |
| 4 | 3.56 | 1.98 | 1.71 |
| 4 | 5.00 | 2.03 | 1.64 |
| 4 | 10.00 | 2.23 | 1.28 |
| 4 | 20.00 | 2.30 | — |
| 4 | 30.00 | 2.21 | — |

Note: Relative volatility is for n-octane with respect to toluene. Equilibrium cell temperatures ranged from 196° to 240° F. (91°–116° C.), depending on the normal boiling point of the mixture. It may be that at the high water levels, the sulfolane solvent may exhibit two phases because of the limited solvency of sulfolane for hydrocarbons.

EXAMPLE III

Vapor-liquid equilibrium data were also obtained using a reformate obtained from a steam-active reformer. Composition was:

| Component | Weight % |
|---|---|
| n-Hexane | 6.51 |
| n-Heptane | 17.07 |
| n-Octane | 8.77 |
| n-Nonane | 0.96 |
| Benzene | 3.78 |
| Toluene | 16.86 |
| Ethylbenzene | 13.87 |
| Xylenes | 15.25 |
| $C_9$ and $C_{10}$ Aromatics | 7.70 |
| Others | 9.23 |

From the phase compositions relative volatilities were calculated for n-octane with respect to benzene ($\alpha_{OB}$) and with respect to toluene ($\alpha_{OT}$).

| | Water in | Relative Volatilities | | | |
|---|---|---|---|---|---|
| | | $\alpha_{OB}$ | | $\alpha_{OT}$ | |
| S/F | Solvent, Wt. % | DPS | Sulfolane | DPS | Sulfolane |
| 1.0 | 4.00 | 0.65 | 0.59 | 1.41 | 1.24 |
| 2.0 | 4.00 | 0.88 | 0.78 | 1.86 | 1.58 |
| 3.0 | 4.00 | 0.96 | 1.00 | 2.13 | 1.94 |
| 4.0 | 4.00 | 1.21 | 1.27 | 2.38 | 2.37 |
| 4.0 | 8.00 | 1.32 | 1.04 | 2.60 | 1.91 |
| 4.0 | 12.00 | 1.41 | 0.85 | 2.72 | 1.63 |
| 4.0 | 20.00 | 1.40 | — | 2.75 | — |

Again it may be observed from the table that DPS solutions generally exhibit higher relative volatilities than sulfolane, with the difference more marked at higher water concentrations. Relative volatilities for DPS solutions apparently peak in the range of 12-20 weight percent water whereas for solfolane they decline with increasing water concentration. Sulfolane at the 4 percent water level does appear to exhibit relative volatilities equal to or slightly higher than DPS at solvent/feed ratios of 3-4, but these high ratios are generally not of commercial importance. It may be that at the high water levels, the sulfolane solvent may exhibit two phases because of the limited solvency of sulfolane for hydrocarbons.

EXAMPLE IV

Vapor-liquid equilibrium data were also obtained for the n-octane-octene-1 system using DPS solvent. From these data relative volatilities for n-octane with respect to octene-1 were calculated.

| S/F | Water in Solvent, Wt. % | α |
| --- | --- | --- |
| 0.0 | — | 0.90 |
| 1.0 | 3.63 | 1.00 |
| 2.0 | 3.63 | 1.06 |
| 3.0 | 3.63 | 1.11 |
| 4.0 | 3.63 | 1.16 |
| 4.1 | 7.00 | 1.15 |
| 4.5 | 14.00 | 1.08 |
| 4.8 | 20.00 | 1.07 |

These data indicate the selectivity of DPS solvent for olefins, even for a difficult mixture such as the $C_8$ system. Water concentrations of 7 percent or more appear feasible for this system, based on the limited data.

EXAMPLE V

Data similar to Example IV were obtained using ethyl propyl sulfone (EPS) as solvent for separating aromatics from non-aromatics in a BTX reformate containing approximately 60 weight percent aromatics. Relative volatilities for non-aromatics with respect to aromatics were calculated.

| S/F | Water in Solvent, Wt. % | α |
| --- | --- | --- |
| 0.0 | — | 2.55 |
| 1.0 | 2.0 | 5.05 |
| 2.0 | 2.0 | 5.80 |
| 3.0 | 2.0 | 7.05 |
| 4.0 | 2.0 | 7.15 |
| 4.0 | 2.6 | 7.36 |
| 4.1 | 3.8 | 7.83 |
| 4.3 | 7.2 | 9.17 |
| 4.6 | 14.3 | 9.30 |

These data indicate that EPS diluted with water also exhibits increasing relative volatilities with water content for the range studied.

Figure 2:
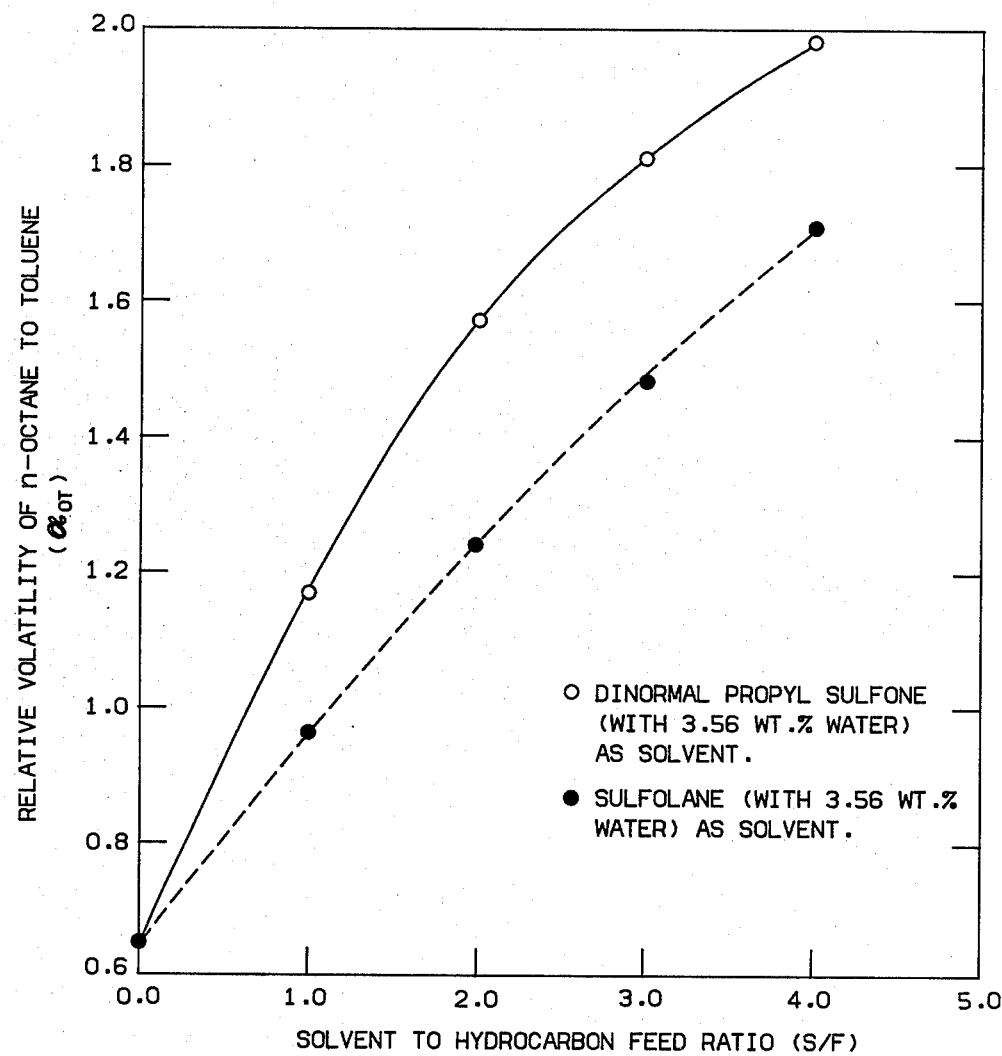
FIG. 2 is a plot of relative volatility versus solvent to hydrocarbon feed ratio.
Figure 3:
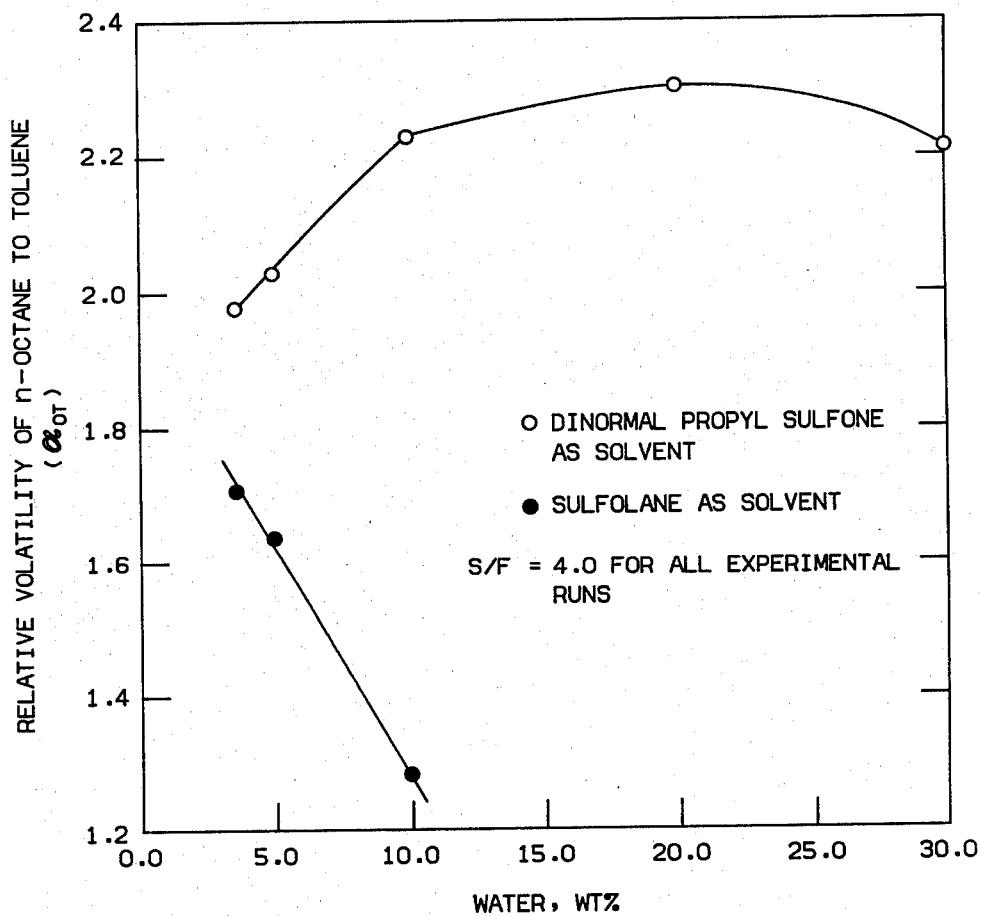
FIG. 3 is a plot of relative volatility versus water content in the solvent.
Figure 4:
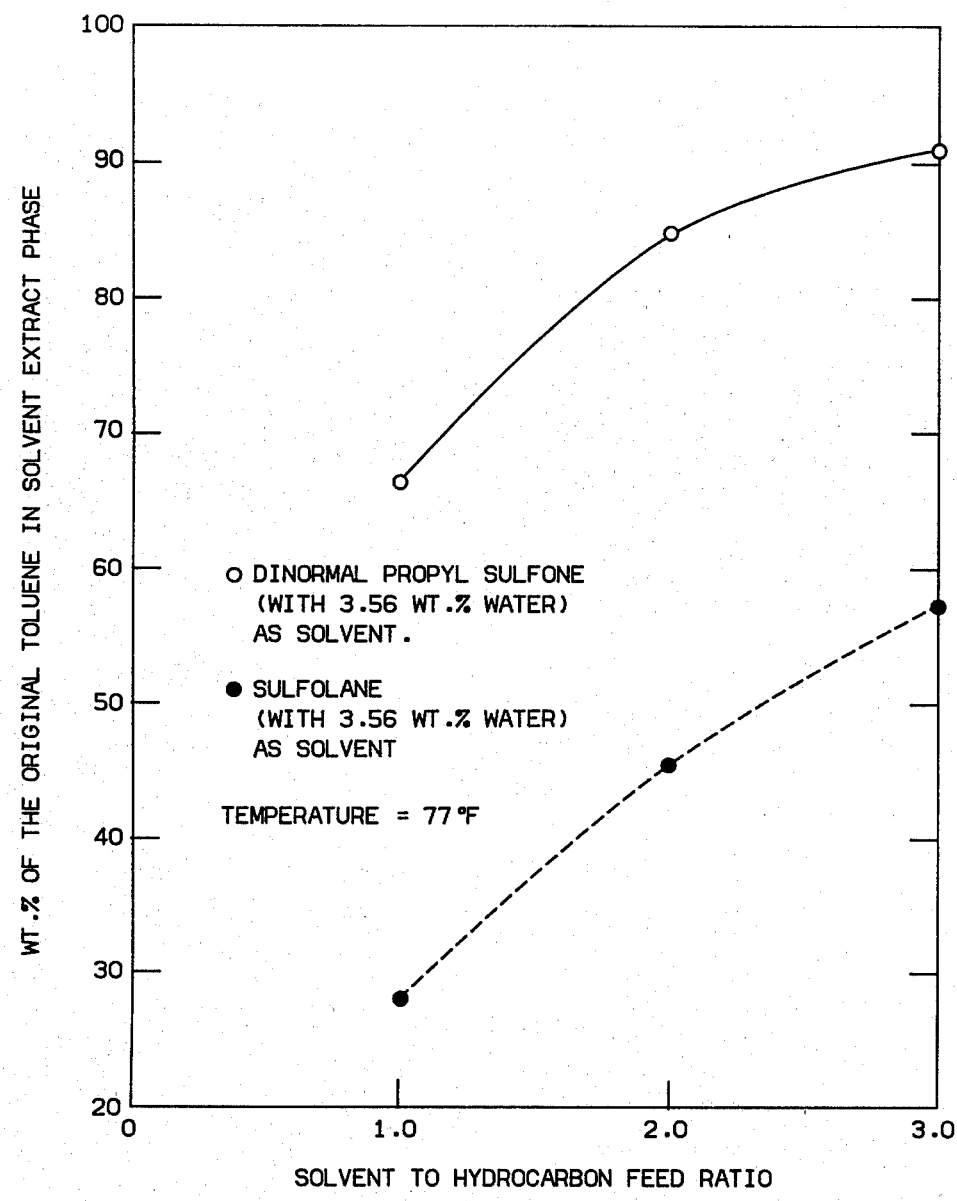
FIG. 4 is a plot of solvency versus solvent to hydrocarbon feed ratio.

The experimental $\alpha_{OT}$ vs S/F and water content of solvent are also presented in FIGS. 2 and 3, respectively. It can be seen that the DPS is more selective than the sulfolane at all solvent to hydrocarbon feed ratios and water contents tested. For example, at S/F=4.0, the maximum $\alpha_{OT}$ for DPS/water solvent was 2.30 at a normal boiling point of 197° F. (92° C.) while the maximum $\alpha_{OT}$ for sulfolane-water solvent was 1.71 at its normal boiling point of 228° F. (109° C.). This means that at near atmospheric pressure the reboiler of an EDC can be operated at about 30° F. lower temperature and simultaneously increase the solvent selectivity by about 35 percent by simply replacing sulfolane-water with polysulfone-water as the selective solvent. The solvency (solubility of toluene) for each solvent versus solvent to hydrocarbon feed ratio is given in FIG. 4. From FIG. 4, it can be observed that the solvency of DPS-water mixture for toluene is 240, 190 and 160 percent of those of sulfolane-water mixtures at the solvent to hydrocarbon feed ratios of 1.0, 2.0 and 3.0, respectively. This greater solvency, of course, makes it possible to make a given separation at lower solvent circulation rates which also means lower energy consumption.

As shown in FIG. 3, the selectivity of sulfolane-water deteriorated very quickly as the water content was increased higher than 3.56 weight percent because of the limited solvency and selectivity of sulfolane. In accordance with the invention, there is the dual advantage of being able to use more water in the solvent which lowers the solvent cost and furthermore the presence of the water lowers the boiling point of the mixture.

Since the boiling point of DPS is 516° F. (269° C.), the separation between hydrocarbons and solvent is very easy and the aromatic products will not be contaminated by the solvent. Excellent thermal stability of DPS at 350° F. (177° C.) makes the inventive solvent system even more attractive because the reboilers of the EDC and stripper will generally be operated below this temperature.

In summary in the above described extractive distillation processes, the dialkyl sulfone/water mixture has higher selectivity and higher solvency than sulfolane-water mixtures and the boiling point of the dialkyl sulfone is sufficiently high so as not to contaminate the hydrocarbon products.

Figure 5:
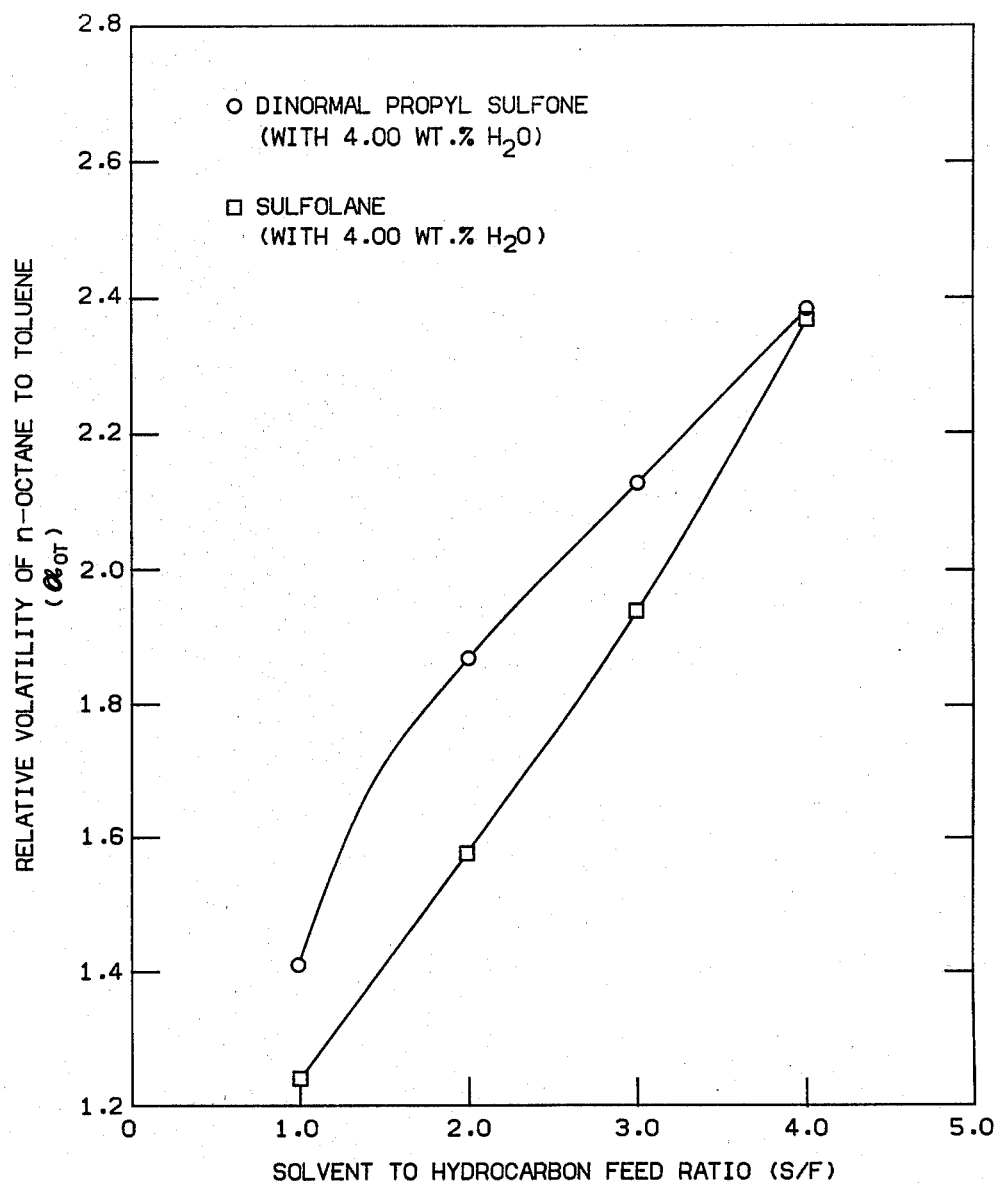
FIG. 5 is a plot of relative volatility of n-octane to toluene versus solvent to hydrocarbon feed ratio.
Figure 6:
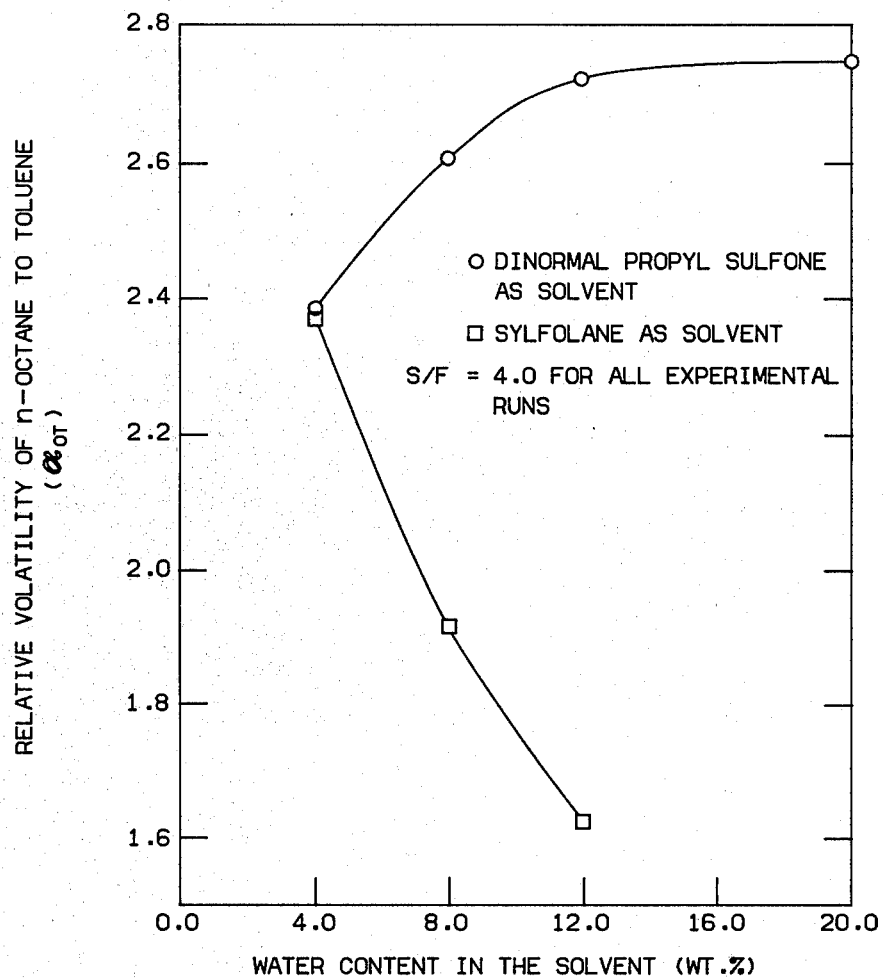
FIG. 6 is a plot of relative volatility versus water content for invention and control solvents.

In order to compare the results of binary and multicomponent hydrocarbon feed, a full range ($C_6$ to $C_9+$) steam active dehydrocyclization reactor effluent (SADHC) used as a multicomponent hydrocarbon feed as depicted in FIGS. 5 and 6 can be compared with FIGS. 1 and 2. This comparison shows that the $\alpha_{OT}$ from the binary system is consistent with that from the multicomponent system.

While this invention has been described in detail for the purpose of illustration, it is not to be construed as limited thereby but is intended to cover all changes and modifications within the spirit and scope thereof.

I claim:

1. A vapor-liquid extractive distillation process comprising:
    introducing a feed comprising at least first and second components of similar boiling points but different solubility characteristics into a substantially vertical extractive distillation zone at a point spaced apart from a lower end of said extractive distillation zone wherein said first component is a non-aromatic hydrocarbon and wherein said second component is an aromatic hydrocarbon;
    introducing into said extractive distillation zone at a point near a top thereof, a solvent comprising a dialkyl sulfone containing 5 to 8 carbon atoms per molecule and at least 1 weight percent water based on the weight of said dialkyl sulfone and said water;
    withdrawing a vaporous raffinate stream rich in said first component from a top portion of said extractive distillation zone; and
    withdrawing an extract stream rich in said second component from a bottom portion of said extractive distillation zone.

2. A vapor-liquid extractive distillation process comprising:

introducing a feed comprising at least first and second components of similar boiling points but different solubility characteristics into a substantially vertical extractive distillation zone at a point spaced apart from a lower end of said extractive distillation zone;

introducing into said extractive distillation zone at a point near a top thereof di-n-propyl sulfone solvent and at least 1 weight percent water based on the weight of said di-n-propyl sulfone and said water;

withdrawing a vaporous raffinate stream rich in said first component from a top portion of said extractive distillation zone; and withdrawing an extract stream rich in said second component from a bottom portion of said extractive distillation zone.

3. A method according to claim 2 wherein said solvent contains 4 to 30 weight percent water.

4. A method according to claim 2 wherein said solvent contains 4 to 20 weight percent water.

5. A method according to claim 2 wherein said feed is a BTX containing stream.

6. A method according to claim 5 wherein said solvent contains 4 to 30 weight percent water.

7. A method according to claim 5 wherein said solvent contains 12 to 20 weight percent water.

8. A method according to claim 7 wherein said extract stream is stripped and solvent recycled to said extractive distillation zone.

9. A method according to claim 1 wherein said sulfone is one of di-n-propyl sulfone and ethyl propyl sulfone.

10. A vapor-liquid extractive distillation process comprising:

introducing a feed comprising a non-aromatic hydrocarbon and an aromatic hydrocarbon of similar boiling points but different solubility characteristics into a substantially vertical extractive distillation zone at a point spaced apart from a lower end of said extractive distillation zone;

introducing into said extractive distillation zone at a point near a top thereof a solvent comprising a dialkyl sulfone containing 4 to 8 carbon atoms per molecule and at least 1 weight percent water based on the weight of said dialkyl sulfone and said water;

withdrawing a vaporous raffinate stream rich in said non-aromatic hydrocarbon from a top portion of said extractive distillation zone; and withdrawing an extract stream rich in said aromatic hydrocarbon from a bottom portion of said extractive distillation zone.

* * * * *